(12) United States Patent
Muta et al.

(10) Patent No.: US 7,064,242 B2
(45) Date of Patent: Jun. 20, 2006

(54) PATCH

(75) Inventors: Kazunori Muta, Tosu (JP); Yasuhisa Kose, Tosu (JP); Masatoshi Kita, Tosu (JP)

(73) Assignee: Hisamitsu Pharmaceuticals Co., Inc., Saga (JP)

( * ) Notice: Subject to any disclaimer, the term of this patent is extended or adjusted under 35 U.S.C. 154(b) by 0 days.

(21) Appl. No.: 10/530,123

(22) PCT Filed: Oct. 3, 2003

(86) PCT No.: PCT/JP03/12694

§ 371 (c)(1),
(2), (4) Date: Apr. 1, 2005

(87) PCT Pub. No.: WO2004/030714

PCT Pub. Date: Apr. 15, 2004

(65) Prior Publication Data

US 2006/0030801 A1 Feb. 9, 2006

(30) Foreign Application Priority Data

Oct. 3, 2002 (JP) .............................. 2002-291717
Jan. 31, 2003 (JP) .............................. 2003-023118

(51) Int. Cl.
*A61F 13/00* (2006.01)
(52) U.S. Cl. ............................ 602/58; 602/41; 602/42; 602/43
(58) Field of Classification Search ............ 602/41–48, 602/52–59; 128/888, 889; 424/443–449
See application file for complete search history.

(56) References Cited

U.S. PATENT DOCUMENTS

2004/0156886 A1* 8/2004 Kose .......................... 424/449
2005/0181163 A1* 8/2005 Kose ......................... 428/40.1

FOREIGN PATENT DOCUMENTS

| EP | 0 993 936 A2 | 4/2000 |
| JP | 60099180 | 6/1985 |
| JP | 08-012954 | 1/1996 |
| JP | 08-291057 | 11/1996 |
| JP | 10-279473 | 10/1998 |
| JP | 2000-072619 | 3/2000 |
| JP | 2000-309764 A | 11/2000 |
| JP | 2001-031563 | 2/2001 |

* cited by examiner

*Primary Examiner*—Kim M. Lewis
(74) *Attorney, Agent, or Firm*—Licata & Tyrrell P.C.

(57) ABSTRACT

A patch comprising a backing layer and a adhesive layer formed on the back face of the backing layer wherein a woven fabric or a nonwoven fabric made of a rayon and pulp fiber mixture is employed as the backing layer and the mixing ratio thereof is from 3:7 to 7:3. When employed in taping a finger, a wrist, an ankle, neck, an elbow, a knee or the like, the patch would not soon curl up or peel off at an overlapping part. After the patch is adhered and then stripped off, no fiber piece remains on the pressure-sensitive adhesive face of the backing layer so that the adhesive force of the patch can be sustained in the case of re-adhesion.

10 Claims, No Drawings

PATCH

TECHNICAL FIELD

The invention relates to a patch. More particularly, it is a water containing patch which is used to the body, hip, arm, leg, face or the like and relates to overlap sticking and/or bandage-type patches which can be used as cosmetics, drugs or quasi-drugs in which it can be taped on a finger, a wrist, an ankle, neck, an elbow and a knee and is not easily curled up and peeled off even when overlapped.

BACKGROUND ART

Conventionally, as a patch have been known a tape agent or a pap agent used for the backache, stiff shoulders, bruise, sprain or the like, a compress agent used for healing fatigue of the foot, eyes or the like and a sheet-like pack agent aiming a figure of the face or the body. An aqueous adhesive composition consisting of polyacrylic acid, polyacrylate, a cellulose derivative, polyalcohol and a polyvalent metal compound (for example, see Patent document 1), a pap agent containing no pharmaceutical ingredient, wherein a moisturizing agent selected from sodium hyaluronate, sodium chondroitin sulfate, lactate, pyrrolidone carboxylic acid, urea, an *aloe* extract and a *perilla* leaf extract is mixed (for example, see Patent document 2), and a sheet agent for a foot care which aims resolution of a foot fatigue or swelling, in which a donating effect of a refreshing feeling or the like by a component in a water-containing adhesive layer is improved and also use feeling is excellent (for example, see Patent document 3), are disclosed. In addition, a drug containing taping-tape, which affects a cooling effect or an analgesic effect by twining an effected area such as a bruise or a sprain in a turn with the protection and fixation (for example, see Patent document 4), and a water-containing sheet-type pack for skin beauty and slimming, wherein the adhesion to the skin is improved by forming a water-containing gel layer on a sheet base having elasticity (for example, see Patent document 5), are disclosed.

Even if the conventional patch was favorable for the adhesiveness to the skin, it was unfavorable for a face except the skin, for example, a fabric face such as a woven fabric or a nonwoven fabric, or even if it was good in adhesiveness, fibers of a backing layer surface stuck to the adhesive layer after it was stripped off once, whereby the adhesiveness in the case of re-adhesion was remarkably lowered and the re-adhesion could not be carried out substantially. In the same way to this, usually a patch containing a drug or the like makes it an aim to stick it to a skin surface, and the adhesiveness to a backing layer face in the case of overlap sticking and/or bandage-type uses of the patch is poor even if the adhesiveness to the skin is sufficient, and is even less in the case that the backing layer is a woven fabric or a nonwoven fabric.

However, in case of taping a finger, a wrist, an ankle, neck, an elbow and a knee by cutting a patch in an appropriate size, only the adhesiveness to the skin is not sufficient, and a patch is desired which is favorable in the adhesiveness to a backing layer face, is easy in adhesively fixing and would not easily curl up and peel off even when it is overlapped. Further, when taping it is not necessarily possible to stick favorably at one time, and the necessity to try again sometimes happens wherefore a patch, in which the initial adhesiveness does not decline even in the case of stripping off after sticking, and the re-adhesion is possible, is firmly desired.

Patent document 1
  JP B 3-16989
Patent document 2
  JP A 8-291057
Patent document 3
  JP A 10-279473
Patent document 4
  JP A 2001-031563
Patent document 5
  JP A 2000-72619

DISCLOSURE OF THE INVENTION

Consequently, the object of the invention is to provide a patch wherein the above conventional problems are solved and when employed in taping a finger, a wrist, an ankle, neck, an elbow, a knee or the like, the patch would not soon curl up or peel off at an overlapping part, and further, after the patch is adhered and then stripped off, no fiber piece remains on the pressure-sensitive adhesive face so that the adhesive force of the patch can be sustained in the case of re-adhesion.

During extensive researches to solve the above problems the inventors employed a sheet-type material such as a woven fabric or a nonwoven fabric of a rayon and pulp fiber mixture as the backing layer, continued further research, found that the above problems can be solved by mixing rayon and pulp in a specific ratio out and accomplished the invention.

Namely, the invention relates to a patch comprising a backing layer and a adhesive layer formed on the back face of the backing layer, wherein the backing layer is a rayon and pulp fiber mixture and the mixing ratio thereof is from 3:7 to 7:3.

In addition, the invention relates to the above patch, wherein at least one part of the backing layer surface and at least one part of the adhesive layer have an overlap sticking part.

Further, the invention relates to the above patch, wherein the adhesive layer has an adhesive force of 0.01–0.5 N/25 mm against the backing layer surface in the overlap sticking part.

Further, the invention relates to the above patch, wherein the adhesive force at the time of re-adhesion of the adhesive layer to the backing layer is not less than ½ of that before stripping off whereby the adhesive layer adhered to the backing layer surface is stripped off after the overlap sticking of the patch.

Further, the invention relates to the above patch, wherein the adhesive force at the time of re-adhesion of the adhesive layer to the backing layer is not less than ⅔ of that before stripping off whereby the adhesive layer adhered to the backing layer surface is stripped off after the overlap sticking of the patch.

Further, the invention relates to the above patch, wherein the adhesive force at the time of re-adhesion of the adhesive layer to the backing layer is not less than ⅘ of that before stripping off whereby the adhesive layer adhered to the backing layer surface is stripped off after the overlap sticking of the patch.

Further, the invention relates to the above patch, wherein the 50% modulus is 30–500 N/25 mm.

Further, the invention relates to the above patch, wherein the adhesive layer contains water.

Furthermore, the invention relates to a bandage comprising the above patch.

In addition, the invention relates to use of the above patch as overlap sticking and/or bandage-type patches.

As described above, the invention is to provide a patch in which the re-adhesion is possible, wherein by employing a sheet-type material such as a woven fabric or a nonwoven fabric of a rayon and pulp fiber mixture as the backing layer and by further making the mixing ratio of these in a specific ratio, its backing layer surface and the adhesive layer can be stuck with overlap, and the initial adhesive force is not largely reduced due to the fact that after removal of the above adhesive layer from the above backing layer surface, a raised nap of fibers of the backing layer surface is little and almost no fiber piece remains on the above adhesive layer.

Therefore, the invention exerts excellent working-effects that even if another patch is adhered with overlap to the backing layer surface, namely, to the opposite face of the face loaded with the adhesive layer, or even if the same patch is adhered to the arm, the leg or the like winding like taping or bandage, it can freely be adhered due to its excellent adhesiveness toward the backing layer surface as a subject, and further, the re-adhesion is possible without remaining of a fiber piece on the adhesive layer.

MODE FOR CARRYING OUT THE INVENTION

The backing layer in the invention consists of a woven fabric or a nonwoven fabric which are constituted by a rayon and pulp fiber mixture, though the nonwoven fabric is preferably selected. By using the rayon and pulp fiber mixture as the backing layer, a pressure-sensitive adhesive agent constituting the patch shows a sufficient sticking effect in the case of adhesion to such backing layer, and further, even in the case of stripping off after adhering the adhesive layer, a raised nap of fibers of the backing layer surface is little and almost no fiber piece remains on the pressure-sensitive adhesive face. That is, in case of adhering the patch of the invention to the arm, the leg or the like with winding like taping or bandage, curling up, peeling off, or falling off from an adhesion part can be prevented, and in case of removing it by the will of a user, a sufficient adhesive force can be secured even if in case of trying adhesion again.

The mixing ratio of rayon and pulp in this fiber mixture is a specifically mixing ratio. Namely, the mixing ratio (weight) between the content of rayon and the content of pulp is preferably from 3:7 to 7:3, more preferably from 4:6 to 6:4. By specifying it in these ranges, the above effect is further promoted, and it is possible to obtain sufficient effects as overlap sticking and/or bandage-type patches. If the ratio of pulp becomes too large, the adhesiveness toward the adhesive layer becomes good, though the backing layer becomes hard, resulting to a tendency of a easy fracture, and if the ratio of rayon becomes too large, the adhesiveness toward the adhesive layer becomes unfavorable, and although it adheres, there is a tendency that the backing layer becomes soft.

By making the mixing amount (weight) of rayon and pulp in the fiber mixture forming the backing layer as the above ratio, a subsequent peeling off can be avoided in case of sticking together so that the adhesive layer is adhered to the backing layer surface of a bandage-type patch of the invention, and further, in the case of stripping off by user's will, the initial adhesive force does not decline due to the fact that a fiber piece is hardly produced from the backing layer surface, and the re-adhesion becomes possible. In addition, it becomes possible to prevent a shape destroying such as a tear due to reduction of a fracture strength of the backing layer.

The adhesive force of the adhesive layer of a bandage-type patch of the invention toward the backing layer surface is preferably 0.01–0.5 N/25 mm in the 180° peel test according to JIS Z0237, more preferably 0.05–0.3 N/25 mm. By making it in such a range, it becomes possible to prevent curling up, peeling off, or falling off in case of adhering a patch of the invention to the human body in a bandage-type use, and further, the re-adhesion after stripping off can sufficiently be kept.

In not more than 0.01 N/25 mm of the adhesive force, a part of the patch has a tendency of stripping off against the will of a user, and in not less than 0.5 N/25 mm of the adhesive force, there is a tendency that it becomes difficult to strip it from the skin according to the will of the user.

Further, in the case that the adhesive layer is adhered with overlap at least to a part of the backing layer surface and stripped off, followed by adhering again the said adhesive layer to the backing layer surface, it is important that as to the patch of the invention the value in the 180° peel test after re-adhesion has the adhesive force of not less than ½ of that before the stripping off, preferably not less than ⅔, more preferably not less than ⅘. Namely, since a raised nap of the backing layer used in the patch of the invention is little and almost no fiber piece derived from the backing layer remains on the adhesive layer, the reduction of the adhesive force in the case of re-adhesion can be made in such range, and after adhering the adhesive layer to the backing layer surface of the invention, the re-adhesion of said adhesive layer to the backing layer surface is possible even in the case of stripping off according to a user's will, and further regardless of the same part or different part of the backing layer. Further, if it has such property, the composition of the pressure-sensitive adhesive agent, etc., are not particularly limited.

In addition, in the patch of the invention, 50% modulus of the patch is preferably 30–500 N/25 mm, more preferably 50–400 N/25 mm. Further, the 50% modulus in the invention is the tensile strength in 50% extension measured by the method according to JIS Z0237.

By making it in such rage, it becomes easy to adhere the patch of the invention to the arm, the leg or the like with winding like taping or bandage, and as described below there is an effect that it is easy to tear it in case of tearing it into an appropriate length by setting a separation line. When the above value is not more than 30 N/25 mm, it is easy to adhere it winding like bandage, and it becomes a tendency that it easily strips off by a recovery power of the patch to the form before the adhesion regardless of user's will. In addition, when it is not less than 500 N/25 mm, the adaptability to the skin becomes poor, and also, it becomes a tendency that it easily strips off regardless of user's will.

As for a bandage-type patch of the invention, the patch may easily be cut in an appropriate length by setting a separation line, perforating or the like in the backing layer and/or adhesive layer of the patch. By having such cutting line, it becomes possible for a user to use it according to a body shape or a part to be adhered, cutting it freely in an appropriate length.

Further, as to a patch of the invention, the stability of the preparation can be secured by applying a adhesive layer on a base fabric consisting of a flexuous backing layer and further laminating a removable film or paper on the surface of this adhesive layer. In addition, as to the removable film or paper, it easily a separation line, perforating or the like are set in order to stick, making a form easy for separation as well as sticking.

Although the color of the backing layer is not particularly limited, it greatly affects an image of a preparation and improves use feeling and an activation feeling to the skin in a greater degree, and white, skin color, yellow, red, orange, green, blue, pink, light blue, brown and the like can be cited, and if necessary a shade is preferably adjusted.

Further, the patch agent of the invention is constituted by the above backing layer and the below base (pressure-sensitive adhesive agent) comprising a removable film or a removable paper. That is, it consists of a constitution comprising a moisturizing agent, water, an aqueous polymer, a cross-linking agent and an antiseptic. In addition, as required, a pharmaceutical ingredient, skin beauty ingredient, moisturizing ingredient, antioxidant, tackifier, dissolution agent, pigment, perfume, surfactant, UV absorber, inorganic filler, pH adjusting agent and the like can be mixed.

As the moisturizing agents, glycols and/or polyalcohols can be used alone or in a combination. The mixing amount of the moisturizing agent based on the total amount of a base is 1–50 wt. %, preferably 5–30 wt. %, and more preferably 5–25 wt. %. In order to prevent lowering of the adhesiveness and cohesiveness of a preparation, lowering of a water holding property and shape retaining property before use, non-uniformity of gel, lowering of productiviy and lowering of use feeling at the time of use, it is desirable to make the mixing amount of the moisturizing agent not less than 1 wt. %. In addition, from the viewpoint of maintaining the adhesiveness and cohesiveness of the preparation, the water holding and shape retaining properties before use, and of preventing lowering of productiviy and lowering of use feeling at the time of use, it is desirable to make the mixing amount not more than 50 wt. %.

Further, the glycols in the moisturizing agent can be used as a dispersion-dissolution agent or a plasticizer for a water-soluble polymer, a moisturizing ingredient, a cross-linking agent, a skin beauty ingredient, an antiseptic and the like, while it can accelerate an evaporation or releasing properties of water.

Since the glycols cited here have a polyether structure and are weak in hydrophilicity due to less hydroxyl groups compared with a low molecular polyalcohol generally used, it is possible to lower a critical relative humidity of base ingredients except water and to release more water to the outside at the time of use. As the result, they give moisture to the skin and also take the heat of vaporization by evaporation of water to the outside, thereby suppress a glow of face and inflammation, and at the same time give a pleasant refreshing feeling. In addition, the temperature dependency of the viscosity is small, whereby they show a stable shape retaining property regardless of an environmental change when mixed in a preparation. As the glycols having a polyether structure, polyethylene glycol of the average molecular weight 200–600 and polypropylene glycol of the average molecular weight 500–3000 are preferable, and one or more of these can be used by mixing.

In addition, the polyalcohos in the moisturizing agent can be used as a dispersion-dissolution agent or a plasticizer for a water-soluble polymer, a moisturizing ingredient, a cross-linking agent, a skin beauty ingredient, an antiseptic and the like, while they can accelerate an evaporation or releasing properties of water. Since the polyalcohols cited here are low-molecular polyalcohols having two or three hydroxyl groups in one molecule and are excellent in hydrophilicity, it is possible to increase a critical relative humidity of base ingredients except water and to inhibit release and evaporation of water to the outside at the time of use. Propylene glycol, 1,3-butylene glycol and glycerin are preferable as the polyalcohos, and one or more of these can be used by mixing. The mixing balance between the glycols and/or the polyalcohols in these moisturizing agents and water gives an appropriate moisturizing and an adhesiveness toward the skin, whereby a comfortable refreshing feeling at the time of sticking is obtained, and the use feeling after stripping off is remarkably improved.

As water, a purified water, a sterile water or a natural water are used. Water acts as a dispersion-dissolution agent for the water soluble polymers, the moisturizing ingredients, the cross-linking agents, the antiseptics and the like, and is particularly important to disperse and dissolve the glycols and polyglycols of the moisturizing agents uniformly in a preparation. Further, water itself increases use feeling during the use and after the use, and moves into the skin together with the moisturizing ingredient, bringing an effect to give moisture and tension. Owing to this, as the mixing amount of water it is necessary to add in 30–95 wt. %, preferably 65–90 wt. %, and more preferably 70–85 wt. % of a large amount. The relative humidity of a preparation itself can be heightened by containing a large amount of water in a preparation, and it becomes possible to drain off effectively a lot of water to the outside, consequently giving moisture to the skin and being able to afford a comfortable refreshing feeling by taking the heat of vaporization by the evaporation of water into the outside. In order to prevent lowering of the adhesiveness of a preparation and of a water holding capacity before use, lowering of productiviy and lowering of use feeling during use, it is desirable to make the mixing amount of water not less than 30 wt. %. In addition, in order to prevent inhibition of the adhesiveness and the cohesiveness as well as and lowering of a shape retaining property before use, it is desirable to make the mixing amount of water not more than 95 wt. %.

Illustrative of the aqueous polymers are gelatin, polyacrylic acids, salts thereof, partial neutralization products thereof or the like, and each can be used individually or by mixing two or more. As salts of polyacrylate, metal salts such as sodium, lithium and potassium are preferable, and one whose average degree of polymerization is 1000–100000 is expediently used. The mixing amount of these aqueous polymers is used in 3–25 wt. %, preferably 5–20 wt. %, and more preferably 5–10 wt. %. In order to maintain the adhesiveness and cohesiveness of a preparation, a shape retaining property, water absorption etc., and to prevent non-uniformity of adhesive mass, lowering of productiviy, and lowering of use feeling, it is desirable to make the mixing amount not less than 3 wt. %. In addition, in order to maintain the adhesiveness and cohesiveness of the preparation, the shape retaining property, and to prevent excessive increase of viscosity during production, non-uniformity of adhesive mass, lowering of productiviy, and lowering of use feeling, it is desirable to make the mixing amount not more than 25 wt. %.

As the cross-linking agents, a slightly water-soluble aluminum compound or a polyfunctional epoxy compound can be used alone or used by mixing two or more. Illustrative of the slightly water-soluble aluminum compounds are aluminum hydroxide, aluminum hydroxide gel, aluminum silicate hydrate, synthetic aluminum silicate, kaolin, aluminum acetate, aluminum lactate, aluminum stearate, magnesium metasilicate aluminate, magnesium silicate aluminate an the like, and one or more of these can be used by mixing. Use of the slightly water-soluble aluminum compounds gives gel an appropriate strength in an initial physical property as a filler in addition to an inhibitory effect for skin irritation by the antacid action and a skin astringent action by trace aluminum ion, and along with this, aluminum ion dissolves into the preparation in a time course, whereby it is possible to show a function to recover the lowering of the gel strength owing to a time dependent decomposition of the polymer and a time dependent cleavage of a cross-linking part of covalent bondings between polymer molecules. Further, the aluminum dissolution rate can be controlled by adjusting pH.

Illustrative of the polyfunctional epoxy compounds are polyethylene glycol diglycidyl ether, ethylene glycol diglycidyl ether, glycerin diglycidyl ether, glycerin triglycidyl ether, propyleneglycol diglycidyl ether, polyglycerol polyglycidyl ether, sorbitol polyglycidyl ether, sorbitan polyglycidyl ether, trimethlolpropane polyglycidyl ether, pentaerythrityl polyglycidyl ether, resorcinol diglycidyl ether, neopentylglycol diglycidyl ether and the like. One or more of these polyfunctional epoxy compounds can be used by mixing. An excellent water absorption and shape retaining properties can be obtained by use of the polyfunctional epoxy compounds, and they can produce covalent bonding with water soluble polymers having a carboxyl, amino or hydroxyl groups, or the like, enhancing a gel strength.

As the mix amount of these crosslinking agents, it is used in 0.05–20 wt. %, preferably 0.5–15 wt. %, and more preferably 1–10 wt. %. From the view point of preventing lowering of the cohesiveness, shape retaining property and water absorption power of a preparation, lowering of a time dependent stability in a physical property of the preparation, lowering of productiviy, lowering of safety for the skin and lowering of use feeling, it is desirable to make the mixing amount not less than 0.05 wt. %. In addition, in order to maintain the adhesiveness and cohesiveness and shape retaining property, and to prevent excessive increase of viscosity during production, non-uniformity of adhesive mass by gelation, lowering of productiviy, lowering of safety for the skin and lowering of use feeling, it is desirable to make the mixing amount not more than 20 wt. %.

Illustrative of the antiseptics are p-hydroxybenzoic acid esters such as methylparaben, ethylparaben and propylparaben, 1,2-pentanediol, benzoic acid, benzoate, salicylate, sorbic acid, sorbate, dehydroacetate, 4-isopropyl-3-methylphenol, 2-isopropyl-5-methylphenol, phenol, hinokitiol, cresol, 2,4,4'-trichloro-2-hydroxydiphenyl ether, 3,4,4'-trichloro-carbanide, chlorobuthanol, benzalkonium chloride and benzethonium chloride, and one or more of these can be used by mixing. The p-hydroxybenzoic acid esters preferable among these. As the mixing amount used is in 0.005–10 wt. %, preferably 0.01–5 wt. %, and more preferably 0.01–1 wt. %. In order to prevent the putrefaction of a preparation by appearance of molds or bacteria during storage and lowering of use feeling when using and after using, it is desirable to make the mixing amount not less than 0.005 wt. %. In addition, in order to prevent delicate change of the adhesiveness and cohesiveness in the preparation, irritation in use feeling, an unpleasant feeling by antiseptic smell, and the like, it is desirable to make the mixing amount not more than 1 wt. %.

The patch agent of the invention can appropriately be mixed in a suitable amount with pharmaceutical ingredients, skin beauty ingredients, moisturizing ingredients, antioxidants, tackifiers, dissolution agents, pigments, perfumes, surfactants, UV absorbers, an inorganic fillers, pH adjusting agents and the like, which are known in themselves, in addition to the above base components.

As the pharmaceutical ingredients, they are not limited particularly if they are percutaneously absorbable drugs, and illustrative of drugs being steroidal anti-inflammatory agents such as prednisolone, dexamethasone, hydrocortisone, fluocinolone acetonide, betamethasone valerate, betamethasone dipropionate, clobetasone butylate and prednisolone succinate, non-steroidal anti-inflammatory agents and ester derivatives such as thereof methyl salicylate, glycol salicylate, indomethacin, ketoprofen, diclofenac, ibuprofen, flurbiprofen, felbinac, ketlolac, loxoprofen, suprofen, pranoprofen, thiaprofen, flufenamic acid, tenidap, aspirin, actirit, mizoribine, oxaprozin, mofezolac, etodolac, auranofin and indmethacin farnesil, antiallergic agents such as tranilast, azelastine, ketotifen, ibudilast, oxatomide, emedastine and epinastine, antihistaminic agents such as diphenhydramine, chlorpheniramine, promethazine and tripelennamine, agents for central nervous system such as chlorpromazine, nirazepam, diazepam, phenobarbital and reserpine, hormones such as insulin, testosterone, norethisterone, methyltestosterone, progesterone and estrdiol, antihypertensive agents such as clonidine, reserpine, guanethidine sulfate, efonidipine, alprenolol and nifedipine, cardiotonic agents such as digitoxin and digoxin, antiarrhythmic agents such as propranolol hydrochloride, procainamide hydrochloride, ajimaline, pindolol and tulobuterol hydrochloride, coronary vasodilators such as nitroglycerin, isosorbide dinitrate, papaverine hydrochloride, nifedipine, diltiazem and nicorandil, local anesthetics such as lidocaine, procaine, procaine hydrochloride, benzocaine and tetracaine, analgesics such as morphine, aspirin, codeine, acetoanilide and aminopyrine, muscle relaxants such as tizanidine, eperisone, tolperisone, inaperisone and dantorolene, antifungal agents such as acetophenylamine, nitroflazone, pentamycine, naphthiomate, miconazole, clotrimazole and butenafine hydrochloride, antineoplastic agents such as 5-fluorouracil, busulfan, actinomycine, bleomycine and mitomycine, urinary incontinence agents such as terodiline hydrochloride and oxybutynin hydrochloride, antiepleptic agents such as nirazepam and meprobamate, antiparkinson agents such as chlorzoxazone, levodopa, amantadine, selegiline hydrochloride, ranolazine hydrochloride and ropinirole hydrochloride, antiemetic agents such as granisetron, azasetron, ondansetron and ramosetron, agents for pollakisuria such as oxybutin, Ca antagonists such as nifedipine, psychotropic agents such as fentanyl, morphine and imipramine, antivertigo agents such as difenidol and betahistine, cardiovascular agents such as bezothiazepin, antituissive-expectorant agemts such as ketotifen, tulobuterol and tranilast, ameliorants of cerebral circulation such as vinpocetine, nicergorine, nicorandil, clentiazem maleate, fasudil hydrochloride, benidipine hydrochloride and efonidipine hydrochloride, agents for cerebrovascular dementia such as docosahexaenoic acid, vinconate hydrochloride and nebracetum fumarate, agents for Alzheimer disease such as donepezil hydrochloride, amiridin hydrochloride and memantine hydrochloride, polypeptide type hormones such as luteonizing hormone-releasing hormone and thyrotropin releasing hormone, immunomodulating agents such as polysaccharides, auranofin and lobenzarit, cholagogue agents such as ursodeoxy cholic acid, diuretic agents such as hydrofulmethiazide, agents for diabetes mellitus such as tolbutamide, antipodagric agents such as colchicine, smoking cessation aid agents such as nicotine, and further, vitamins, prostaglandins, exitation-analeptic agents, hypnotic-sedative agents, autonomic agents, peripheral vasodilators, or the like.

As the skin beauty ingredients, illustrative are allantoin, glycyrrhizic acid, yeast extract, dried seawater, salt, anhydrous caffeine, l-menthol, dl-menthol, dipotassium glycyrrhizinate, papain enzyme, L-arginine, arbutin, flavonoid, collagen, yogurt extract, lecithin, ellagic acid, amino acids, kojic acid, proteins, saccharides, hormones, placenta extracts such as water-soluble placenta extract, silk or silk extract, or extraction ingredients from various crude drugs such as *aloe*, loofah and *glycyrrhia*, or plant extracts such as *Angelica keiskei* extract, *aspalathus linearis* extract, gambir extract, avogado extract, sweet hydrangea extract, *Gynosstemma pentaphyllum* extract, marshmallow extract, *arnica* extract, almond extract, *aloe* extract, benzoin extract, chestnut rose extract, Japanese knotweed extract, *ginkgo* extract, nettle extract, *iris* root extract, oolong tea extract, fennel extract, turmeric extract, rose fruit extract, Siberian ginseng extract, echinacea leaf extract, green pea extract, *scutellaria* root extract, phenodendron bark extract, goldthread extract, milk thistle extract, *Lagestroemia* extract, barley extract, fermented barley extract, okura extract, hypericam extract, white dead-nettle extract, prickly restharrow extract, watercress extract, orange extract, orange flower extract, seaweed extract, persimmon tannin, *pueraria* extract, valerian extract, cattail extract, annual chamomile extract, annual chamomile water, wild oat extract, chinese quince extract, carrot extract, *Arthemisia capllaris* extract, glycyrrhiza extraction liquid, raspberry extract, *ginkgo* nut extract, banaba tea extract, pagoda extract, buckwheat extract, neroli extract, *magnolia* extract, red-berried elder extract, *hibiscus* extract, cowberry extract, Japanese angelica-tree extract, guavaphenone, sophora root, feather cockscomb, muccuna extract, melosuria extract, lilybulb extract, rasberry extract, lumpuyan, green tea extract, applephenone, Japanese *angelica* root extract, apricot extract, tea tree extract, peach extract, macademia oil, almond oil, kiwi extract, *cinchona* extract, cucumber extract, apricot extract, quince seed extract, *gardenia* extract, Veith's bamboo extract, cumin extract, *Sophora flavescens* extract, walnut pod extract, grape fruit extract, *clematis* extract, *chlorella* extract, mulberry extract, mulberry leaf extract, *mucuna* bird woodiana tutcher extract, cinnamon extract, yellow *gentian* extract, crane's-bill extract, Japanese raisin tree extract, coffee extract, black tea extract, *nuphar* extract, burdock extract, wheat germ extract, rice bran extract, fermented rice bran extract, comfery extract, asiasarum extract, saffron extract, soapwort extract, *crataegus* fruit extract, Japanese pepper extract, shiitake extract, Chinese foxglove extract, *lithospermum* extract, *perilla* extract, Japanese linden extract, meadowsweet extract, peony extract, Job's-tears extract, ginger extract, sweet flag root extract, white birch extract, white birch sap, Japanese honeysuckle extract, horsetail extract, *stevia* extract, sage extract, sage water, common ivy extract, *crataegus* extract, red-berried elder extract, common juniper extract, yarrow extract, peppermint extract, mallow extract, celery extract, *cnidum* rhizome extract, *cnidum* rhizome water, sialid extract, soybean extract, jujube extract, thyme extract, tea extract, tea nut extract, clove tree extract, polyporus *sclerotium* extract, *citrus unshiu* peel extract, *camellia* extract, *centella* extract, duke extract, *terminalia* extract, tian cha extract, bunincasae semen extract, Japanese amgelica root extract, marigold extract, Japanese amgelica root water, vegitative wasp extract, peach kernel extract, orange peel extract, corn extract, dokudami extract, tomato extract, *P. tormentilla* schoran k. extract, fermented soybean extract, *ginseng* extract, garlic extract, wild rose extract, malt extract, ophiopogon tuber extract, parsley extract, distilled mint water, rugosa rose extract, witch-hazel extract, witch-hazel extraction liquid, rose extract, *parietaria* extract, *Plectranthus japonicus* extract, cypress water, white sandalwood extract, loquat leaf extract, coltsfoot extract, tuckahoe extract, butcherbroom extract, grape extract, grape water, grape leaf extract, Siebold's beech extract, prune extract, hayflower extract, loofah extract, loofah water, safflower extract, peony extract, hop extract, pine extract, *jasmunum sambac* extract, milk thistle extract, horse chestnut extract, Chinese soapberry extract, *Swertia pseudochinesis* extract, murayaco enzy extract, lemon balm extract, melilot extract, peach leaf extract, bean sprouts extract, cornflower extract, cornflower water, *euclyptus* extract, *euclyptus* water, strawberry saxiflage extract, *Citrus junos* extract, lily extract, *coix* extract, mugwort extract, mugwort water, lavender extract, lavender water, blue-green algae extract, green tea extract, apple extract, apple water, *litchi* extract, lettuce extract, lemon extract, *lotus* flower extract, rosemary extract, rosemary water, rose water, camomile extract, logwood extract or great burnet extract, or vitamin A, vitamin C, vitamin D, vitamin E and the other vitamins, or vitamin C derivatives such as magnesium ascorbic acid phosphate, sodium ascorbic acid phosphate or ascorbic acid-2-glycoside, or the like. Further, illustrative of drugs having a skin-whitening action are diphenhydramine hydrochloride, diphenhydramine salycilate, diphenhydramine tannate, triprolidine hydrochloride, mequitazine, chlorpheniramine maleate, d-chlorpheniramine maleate, clemastine fumarate, promethazine hydrochloride, tranilast, sodium cromoglycate, ketotifen, arylsulfatase B, bufexamac, bendazac, butyl flufenamate, ibuprofen piconol, indomethacin, aspirin, flurbiprofen, ketoprofen, piroxicam, 2-pyridinemethyl mefenamic acid, 5,6-dehydroarachidonic acid, 5,6-methano-LTA4, esculetin, eupatilin, 4-demethyl eupatilin, caffeic acid or benoxaprofen, and one or more of these can be mixed for use.

As the moisturizing ingredients can be mixed one or more of natural moisturizing factors such as aqueous succinyl kefiran solution, aqueous acetyl kefiran solution, aqueous maleyl kefiran solution, malt root extract, rose fruit extract, orange extract, orange juice, raspberry extract, kiwi extract, cucumber extract, *gardenia* extract, grape fruit extract, *crataegus* fruit extract, Japanese pepper extract, *crataegus* extract, common juniper extract, zizyphi fructus extract, jujube extract, duke extract, tomato extract, grape extract, loofah extract, lime juice, apple extract, apple juice, lemon extract, lemon juice, *perilla* extract, mulberry bark extract, marshmallow extract, horse-chestnut extract, moutan bark extract, *Coix lachryma-jobi* extract, olive oil, oligomer, chitin, chitosan, wheat germ extract, rice bran extract, jujube, hyaluronic acid, vitamin A, jojoba oil, whitelupin, linoleic acid, quince seed extract, royal jelly, rose extract, annual chamomile extract, *aloe*, carrot extract, β-carotene, red grape extract, lemon balm extract, squalene, silk protein, collagen, sodium hyaluronate, sodium bio-hyaluronate, trehalose, litchi extract, black tea extract, *chlorella* extract, yeast extract, soybean extract, garlic extract, mugwort extract, *aloe* extract, seaweed extraction liquid, trimethylglycine, saccharides such as sorbitol, L-proline and sodium pyrrolidonecarboxylate. Further, fruit extracts (fruit juices) have action effects as a perfume.

As the antioxidants can be mixed ascorbic acid, propyl gallate, butylhydroxyanisol, dibutyl hydroxy toluene, nordihydroguaretic acid, tocopherol, tocopherol acetate, natural vitamin E and the like.

As the tackifiers can be mixed casein, pullulan, agar, dextran, sodium aluginate, soluble starch, carboxystarch, dextrin, carboxymethyl cellulose, sodium carboxymethyl cellulose, methylcellulose, ethylcellulose, hydroxyethylcellulose, polyvinyl alcohol, polyethylene oxide, polyacrylamide, polyacrylic acid, polyvinylpyrrolidone, carboxyvinyl polymer, polyvinyl ether, polymaleic acid copolymer, meth oxyethylene maleicanhydride copolymer, isobutylene maleicanhydride copolymer, polyethylene imine, polyvinyl alcohol partial hydrolysate, hydoxypropylmethyl cellulose, xanthan gum, poly-N-vinylacetamide and the like.

As the dissolution agents can be mixed benzyl alcohol, pyrothiodecane, peppermint oil, isopropyl mirystate, crotamitone and the like.

As the pigments can be mixed the officially designated pigments such as Red No. 2 (amarnath), Red No. 3 (erythrosine), Red No. 102 (new coccine), Red No. 104-1 (phloxine B), Red No. 105-1 (rose bengale), Red No. 106 (acid red), Yellow No. 4 (tartrazine), Yellow No. 5 (sunset yellow FCF), Green No. 3 (fast green FCF), Blue No. 1 (brilliant blue FCF), Blue No. 2 (indigo carmine) and the like. As for the pigments they are not particularly limited, though they give a big influence to a preparation image and result to the improvement of use feeling and an activation feeling to the skin.

As the surfactants can be mixed an anionic surfactant such as sodium dioctyl sulfosuccinate, alkylsulfate, 2-ethylhexyl alkylsulfate sodium salt or sodium n-dodecyl benzenesulfonate, a cationic surfactant such as hexadecyl trimethylammonium chloride, octadecyl dimethyl benzyl ammonium chloride or polyoxyethylene dodecyl monomethylammonium chloride, and a nonionic surfactant such as polyoxyethylene stearylether, polyoxyethylene tridecylether, polyoxyethylene nonylphenylether, polyoxyethylene octylphenylether, polyoxyethylene monostearate, sorbitan monostearate, sorbitan monopalmitate, sorbitan sesquioleate, polyoxyethylene sorbitan monolaurate, polyoxyethylene sorbitan monooleate, glycerol monostearate, polyglycerin fatty acid ester, polyoxyethylene octadecyl amine or polyoxyethylene hardened castor oil.

As the UV absorbers can be mixed p-aminobenzoic acid, p-aminobenzoic acid ester, amyl p-dimethylaminobenzoate, salicylic acid ester, methyl anthranilate, umbelliferone, esculin, benzyl cinnamate, cinoxate, guaiazulene, urocainic acid, 2-(2-hydrozxy-5-methylphenyl)benzotriazole, 4-methoxybenzophenone, 2-hydroxy-4-methoxy benzophenone, dioxybenzone, octabenzone, dihydroxy dimethoxybenzophenone, slisobenzone, benzoresorcinol, octyl p-dimetylaminobenzoate, ethylhexyl p-methoxycinnamate, or the like.

As the inorganic fillers can be mixed titanium oxide, talc, zinc oxide, silicate hydrate, magnesium carbonate, dibasic calcium phosphate, magnesium silicate, diatomaceous earth, anhydrous silicic acid, bentonite or the like.

As the pH adjusting agents can be mixed acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, diprpopanolamine, trimethanolamine, triethanolamine, tripropanolamine, citrate buffer, phosphate buffer, glycine buffer, acetate buffer, other buffer or the like.

The pH of the base appropriately mixed in a suitable amount of each of the above components is to be considered not to give irritation to the skin, and the pH of the base is preferably in the range of 4–8, more preferably 5–7.

As a process for preparing the patch of the invention, the above components are uniformly mixed and/or dissolved in a stirring apparatus and spreaded on the above backing layer of non-dyeing or dyeing, thereon a stripping paper is stuck, and it is appropriately cut in a fixed shape. That is, aiming to use in a part of the face or the body it can be processed into a shape to apply well to aimed parts such as for the breast, back, arm, foot, hip, shoulder, elbow, neck, finger, wrist, ankle, neck, face, nose, eye-around or the like. Further, the patch of the invention is desirably preserved in a sealed bag or container until use from the viewpoint that contamination under preservation, decrease of effectiveness by the evaporation of a volatile substance or the like are prevented.

EXAMPLE

In the following, the patch of the invention is explained in more detail by the example and test examples. However, the invention is not limited in any way by these.

(Example)

Purified water 79.02 wt. %, gelatin 0.5 wt. %, methylparaben 0.2 wt. %, propylparaben 0.05 wt. %, propylene glycol 5 wt. %, glycerin 5 wt. %, ethylene glycol diglycidyl ether 0.02 wt. %, partially neutralized polyacrylic acid 5 wt. %, dipotassium glycyrrhizinate 0.1 wt. %, tocopherol acetate 0.1 wt. %, aluminum acetate 0.01 wt. % and synthetic aluminum silicate 5 wt. % were stirred till a homogenous dispersion and dissolution mixture. Subsequently, the mixture was spreaded on a backing layer to make it in the proportion of 714 g/m$^2$ and was stuck with film. Then, it was cut into 5 cm×20 cm to afford the patch. The backing layer used in the example 1 is rayon:pulp=4:6.

(Test Example 1) 180° Peel Test in Overlap Sticking of Backing Layer Surface and Adhesive Agent Face (180° Adhesive Force)

The test was carried out in principle according to JISZ0237. The test conditions are shown in the following.

| (Test atmosphere) | |
| --- | --- |
| Room temperature | 23 ± 2° C. (Observed 25° C.) |
| Relative humidity | 50 ± 5% (Observed 55%) |

(Test Piece)

A sample of the example with product size 50 mm×100 mm is adhered to a stainless-steel test board 50×125 mm, and further, a sample cut in 25 mm width×100 mm length is adhered with overlap. Here, one side of the sample 25 mm width×100 mm length was stuck together with a paper tape 25 mm×100 mm so that 25 mm×25 mm area overlapped. Further, using a pressure-adhesive apparatus the pressure adhesion was carried out under the condition of the pressure-adhesive velocity 300 mm/min (=5 mm/sec)×1 reciprocation, and the measurement was made after standing it for 5 min. In addition, as to the second time, the third time and the fourth time stpeel tests, the measurements were repeatedly made using the same sample under the same condition. Each test was carried out three times, and the mean value was calculated. The results are shown in Table 1.

(Used Machine)
TENSILON RTA-100 manufactured by ORIENTEC

| | (Test velocity) 300 mm/min |
|---|---|
| Stripping times | 180° Adhesive force (adhesive strength of backing layer/ pressure-sensitive adhesive agent) |
| First time | 0.1190 (N)/25 mm |
| Second time | 0.1256 (N)/25 mm |
| Third time | 0.1218 (N)/25 mm |
| Fourth time | 0.1442 (N)/25 mm |

(Test Example 2) 50% Modulus Test of Preparation

The test was carried out in principle according to JISZ0237. As to the sample of the example, each sample was measured three times under the following condition and the mean value was calculated.

| 50% Modulus | Long side direction | 126.77 N/25 mm |
|---|---|---|
| | Short side direction | 328.17 N/25 mm |
| | (Test atmosphere) | |
| Room temperature | 23 ± 2° C. (Observed 25° C.) | |
| Relative humidity | 50 ± 5% (Observed 55%) | |

(Test Piece)

The product size 50 mm×100 mm was cut into the long side (25 mm width×100 mm length) and the short side (25 mm width×50 mm length) and used.

(Used Machine)
TENSILON RTA-100 manufactured by ORIENTEC (Initial Sample Length: Grasping Space)
30 mm (Test Velocity)
300 mm/min

INDUSTRIAL APPLICABILITY

The invention is able to provide a patch, wherein by employing a woven fabric or nonwoven fabric of a rayon and pulp fiber mixture as the backing layer and by making the mixing ratio of these in a specific ratio, its backing layer surface and the adhesive layer can be stuck with overlap, and the initial adhesive force is not largely reduced due to the fact that after the stripping off a raised nap of fibers of the backing layer surface is little and almost no fiber piece of the backing layer remains on the adhesive layer, whereby there-adhesion is possible. Therefore, the invention exerts excellent working-effects that even if another patch is adhered with overlap to the backing layer surface, namely, to the opposite face of the face loaded with the adhesive layer, and even if the same patch is adhered winding like taping or bandage, it can freely be adhered due to an excellent adhesiveness toward the backing layer surface as a subject, and the re-adhesion is possible, is industrially very useful.

What is claimed is:

1. A patch comprising a backing layer and an adhesive layer formed on the back face of the backing layer wherein the backing layer is a rayon and pulp fiber mixture and the mixing ratio thereof is from 3:7 to 7:3.

2. The patch according to claim 1, wherein at least one part of the backing layer surface and at least one part of the adhesive layer have an overlap sticking part.

3. The patch according to claim 1, wherein the adhesive layer has an adhesive force of 0.01–0.5 N/25 mm against the backing layer surface in the overlap sticking part.

4. The patch according to claim 1, wherein the adhesive force at the time of re-adhesion of the adhesive layer to the backing layer is not less than ½ of that before stripping off whereby the adhesive layer adhered to the backing layer surface is stripped off after the overlap sticking of the patch.

5. The patch according to claim 1, wherein the adhesive force at the time of re-adhesion of the adhesive layer to the backing layer is not less than ⅔ of that before stripping off whereby the adhesive layer adhered to the backing layer surface is stripped off after the overlap sticking of the patch.

6. The patch according to claim 1, wherein the adhesive force at the time of re-adhesion of the adhesive layer to the backing layer is not less than ⅘ of that before stripping off whereby the adhesive layer adhered to the backing layer surface is stripped off after the overlap sticking of the patch.

7. The patch according to claim 1, wherein the 50% modulus is 30–500 N/25 mm.

8. The patch according to any one of claim 1, wherein the adhesive layer contains water.

9. A bandage comprising the patch according to claim 1.

10. A method of use of the patch according to claim 1 as overlap sticking and/or bandage-type patches comprising the step of applying the patch to the user.

* * * * *